United States Patent [19]

Miura et al.

[11] Patent Number: 4,827,736
[45] Date of Patent: May 9, 1989

[54] CRYOGENIC REFRIGERATION SYSTEM FOR COOLING A SPECIMEN

[75] Inventors: Kazuo Miura, Nara; Yoon M. Kang, Sakai; Shoichi Taneya, Sakai; Satoshi Noguchi, Sakai; Katsumi Sakitani, Kawachinagano, all of Japan

[73] Assignee: Daikin Industries, Ltd., Osaka, Japan

[21] Appl. No.: 215,531

[22] Filed: Jul. 6, 1988

[51] Int. Cl.⁴ .............................................. F25B 19/00
[52] U.S. Cl. .......................................... 62/51.1; 62/6; 62/78; 62/55.5
[58] Field of Search ....................... 62/6, 55.5, 78, 51.1

[56] References Cited

U.S. PATENT DOCUMENTS

| | | | |
|---|---|---|---|
| 4,363,217 | 12/1982 | Venuti | 62/55.5 |
| 4,563,883 | 1/1986 | Sitte | 62/514 R |
| 4,565,925 | 1/1986 | Anderson et al. | 62/514 R |
| 4,578,963 | 4/1986 | Sitte | 62/514 R |
| 4,745,761 | 5/1988 | Bazaj et al. | 62/55.5 |
| 4,751,828 | 6/1988 | Coulter et al. | 62/514 R |

FOREIGN PATENT DOCUMENTS 58-214758  12/1983  Japan.

Primary Examiner—Ronald C. Capossela
Attorney, Agent, or Firm—Stevens, Davis, Miller & Mosher

[57] ABSTRACT

A cryogenic refrigeration system for cooling specimen, wherein an expander having one or more heat stations and a cooler at a main refrigeration circuit, which has a specimen mounting unit and is cooled at a temperature lower than the heat station, are housed in first and second vacuum chambers separate from each other, and at the second vacuum chamber is provided an open-close lid which is open to enable a specimen to be taken in or out, whereby the second vacuum chamber only is broken of its vacuum so as to enable the specimen to be exchanged.

9 Claims, 4 Drawing Sheets

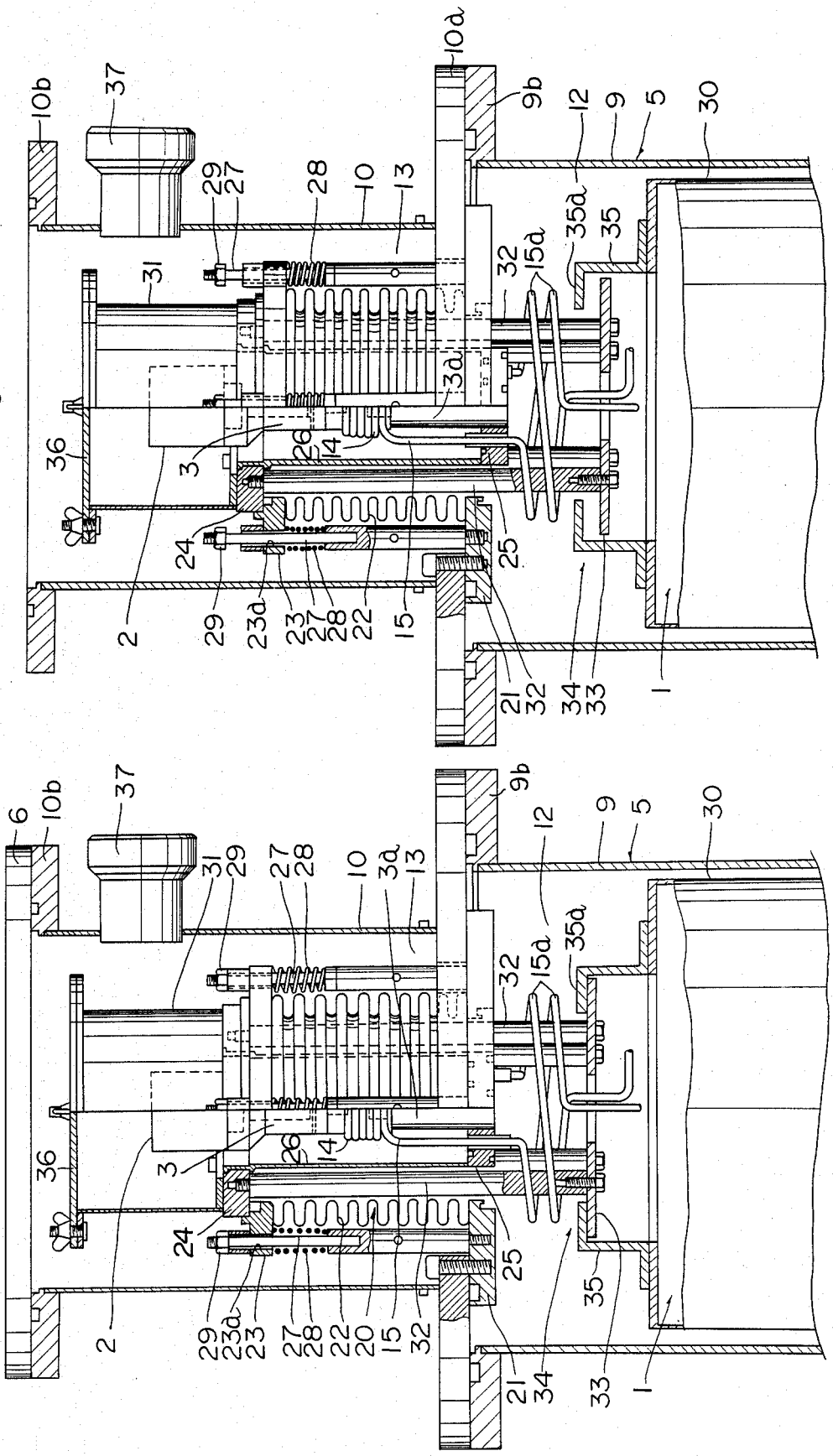

CRYOGENIC REFRIGERATION SYSTEM FOR COOLING A SPECIMEN

FIELD OF THE INVENTION

The present invention relates to a cryogenic refrigeration system for cooling various specimens, such as a super conductive element of Josephson element, a cryogenic thermometer, or an electromagnetic wavemeter, at a cryogenic level of the absolute temperature of several K to several tens K, thereby measuring physical quantities of the specimens.

BACKGROUND OF THE INVENTION

The conventional cryogenic refrigeration system is well-known by the Japanese Patent Laid-Open Gezette No. Sho 58-214,758, which expands high pressure gas, such as helium, in a refrigeration unit by moving a displacer having a hold over, thereby obtaining a very low temperature at a heat station adjacent to an expansion space of the gas.

Generally, this kind of cryogenic refrigeration system, as shown in FIG. 9, uses a low temperature expander EX having a plurality of heat stations H1, H2 and H3 to stepwise lower the cryogenic level, utilizes as a specimen mounting unit X2 the heat station H3 at the lowest temperature level provided at the end of the expander EX, and mounts a specimen, such as a super conductive element or a cryogenic thermometer, on the specimen mounting unit X2, thereby measuring various physical quantities.

The low temperature expander EX and specimen mounting unit X2 are contained in a vacuum container VC, thereby being heat-insulated from the atmosphere.

Furthermore, around the lowest temperature heat station H3 and specimen mounting unit X2 is disposed a thermal shield HS extending from the heat station H1 at the low-temperature expander EX, thereby shielding the specimen mounting unit X2 from heat radiation caused by the vacuum container VC in contact with the stmosphere and further demonstrating the adiabatic effect.

The aforesaid conventional refrigeration system, however, contains both the specimen mounting unit X2 and low temperature expander EX in one vacuum container VC, whereby, when a lid CA is open to exchange the specimen, a vacuum must be broken not only around the specimen mounting unit X2 but also around the low-temperature expander EX. Therefore, all the heat stations H1 through H3, as shown by the broken lines in FIG. 5, are required to raise the temperature up to substantially room temperature so as not to condence moisture in the atmosphere. Also, all the heat stations H1 through H3 after exchanging the specimen are required to be cooled down to a very low temperature, thereby taking much time for carrying out warm-up and cool-down.

In other words, when the specimen is exchanged, the entire vacuum container VC is broken of its vacuum and the first and second heat stations H1 and H2 as well as the specimen mounting unit X2 and third heat station H3, rise at the ambient temperature. A warming-up time until the temperature rise is finished, as shown by the broken line in FIG. 5, takes an extra time required to raise the ambient temperature of the first and second heat stations H1 and H2. When the lid CA is closed after exchanging the specimen and the vacuum container VC gets a vacuum to be cooled, the ambient temperature of the respective heat stations H1 through H3 is raised up to the room temperature, whereby it takes much time from a start to a finish of cooling down the heat stations.

Accordingly, all the heat stations as well as the specimen mounting unit X2 at the low temperature expander EX must be warmed or cooled, whereby energy is consumed in vain and the exchange of specimen takes much time, thereby creating the defect that the specimen cannot be frequently exchanged.

SUMMARY OF THE INVENTION

A main object of the invention is to provided a cryogenic refrigeration system for cooling a specimen, which can solve the above problem, reduce the warm-up and cool-down time, and expect an improvement in actual working efficiency of the refrigeration system.

In detail, the present invention aims at provision of a cryognic refrigeration system which isolates in an airtight manner a vacuum container housing therein a low temperature expander, so that, when the specimen is exchanged, only a vacuum chamber housing therein a cooling unit having the specimen mounting unit is broken of its vacuum, thereby reducing the warm-up and cool-down time.

Another object of the invention is to provide a cryogenic refrigerator system in which the main body of the low temperature expander is less affected by a temperature rise at the cooling unit housed in the vacuum container whose vacuum is broken when the specimen is exchanged.

The present invention is characterized in that the cryogenic refrigeration system for cooling a specimen is provided with: an expander having one or more heat stations and generating coldness by expanding a refrigerant gas, thereby cooling the heat stations by the coldness to hold the same at a predetermined temperature level; a main refrigerating circuit including a cooler having a specimen mounting unit which mounts thereon the specimen and cooling the specimen mounted on the specimen mounting unit and a heat exchanger (to be hereinafter called the precooler) for the refrigerant gas heat-exchanging at the heat station of the expander to obtain the coldness, so that the refrigerant gas obtaining the coldness by the precooler is transferred to the cooler to thereby cool the cooler to the cryogenic level, thereby maintaining the specimen mounted on the specimen mounting unit at the cryogenic level; a first vacuum chamber housing therein the expander; and a second vacuum chamber separate from the first vacuum chamber and housing the cooler and specimen mounting unit at the main refrigeration circuit and provided with an open-close lid which is open to enable the specimen to be taken in or out with respect to the specimen mounting unit.

Thus, when the open-close lid is open to take the specimen in or out of the specimen mounting unit, the first vacuum chamber maintains its vacuum and the second vacuum chamber only is broken of its vacuum, thereby minimizing a spatial volume to break vacuum. Also, the specimen mounting unit need only be warmed or cooled, thereby reducing its warm-up time and cool-down time.

The present invention is further characterized in that the second vacuum chamber is provided with a thermal shield enclosing the cooler and specimen mounting unit at the main refrigeration circuit and thermally connecting to the heat station at the expander, and that between the thermal shield and the heat station of the expander is provided a thermal switch which cuts off the thermal connection of the thermal shield with the heat station at the expander when the open-close lid is open to take in or out the specimen.

Accordingly, the thermal shield provided as above-mentioned can eliminate an adverse effect caused by heat radiation from the exterior to thereby improve adiabatic property. Meanwhile, when the second vacuum chamber breaks its vacuum for exchanging the specimen, the heat transfer from the thermal shield to the heat station at the expander may warm in vain the heat station, but the present invention is provided between the thermal shield and the heat station or a thermal shield provided thereat with the thermal switch which selectively cuts off the thermal connection therebetween, thereby avoiding thermal conduction from the thermal shield to the heat station and reducing the cool-down time.

Other objects and advantages of the present invention will be apparent from the following description of the embodiments with reference to the accompanying drawings.

BRIEF DESCRIPTION OF THE DRAWINGS

FIGS. 3 and 4 are partially enlarged sectional views of the first embodiment in FIG. 2.

DETAILED DESCRIPTION OF THE INVENTION

Figure 2:
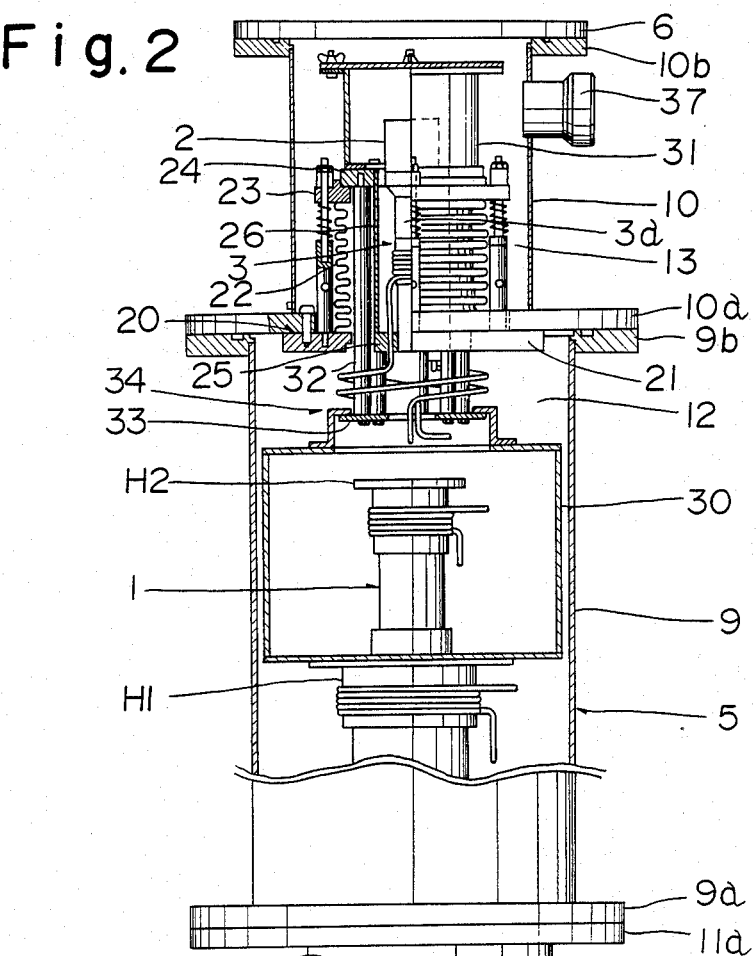
FIG. 2 is a sectional view of a first embodiment of the cryogenic refrigeration system of the invention, showing the principal portion thereof only.

Referring to FIG. 2, an expander 1 having first and second heat stations H1 and H2, a specimen mounting unit 2 cooled at a lower temperature than the seocnd heat station H2 lower at the temperature than the first one H1 and included in a main refrigerating circuit, and a refrigeration stage (to be hereinafter called a cooler) 3 included therein and attached to the specimen mounting unit 2, are housed in one vacuum chamber 5 having an open-close lid which is open to enable the specimen to be taken in or out of the container 5 with respect to the specimen mounting unit 2.

Figure 1:
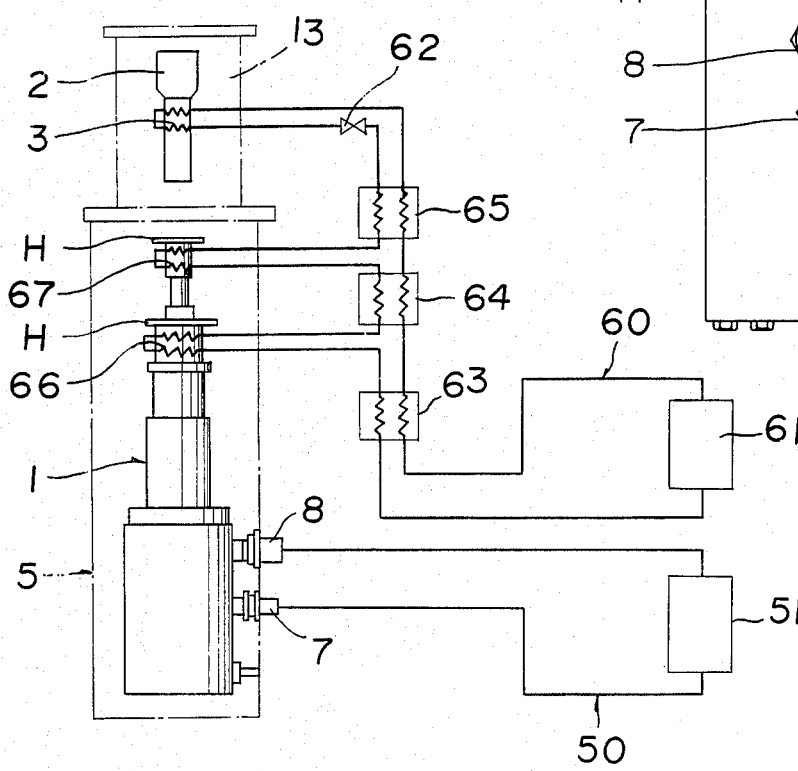
FIG. 1 is a pipe line system diagram of a cryogenic refrigeration system of the invention.
Figure 9:
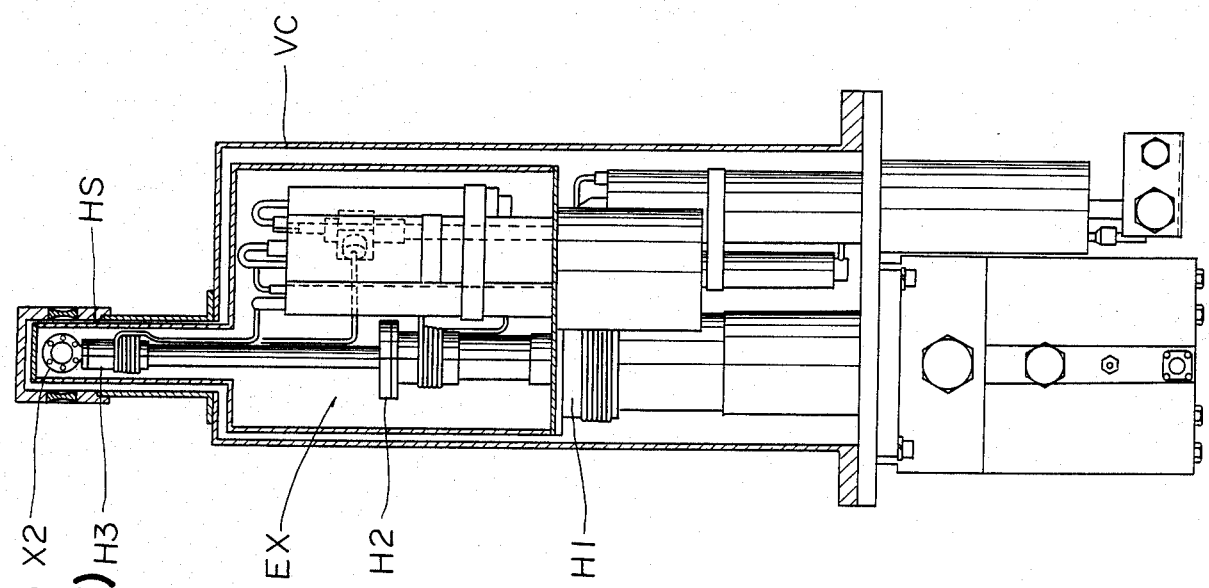
FIG. 9 is a sectional view of the conventional cryogenic refrigeration apparatus.

The expander 1 is schematically shown in FIG. 1, and as disclosed in the Japanese Patent Laid-Open Gazette No. Sho 58-214758, is provided with an inlet 7 for high pressure gas, such as helium gas discharged from a precooling compressor 51, and an outlet 8 for low temperature gas produced by expansion to be discussed below. The high pressure gas is introduced from the inlet 7 into a displacer (not shown) through a rotary valve provided in the expander 1 and driven by a motor, the displacer is moved by pressure of the high pressure gas so as to form an expansion space therefor, and after the gas expansion cools the first heat station H1, the second hear station H2 is cooled. Thus, the first and second heat stations H1 and H2 are sequentially stepwise cooled to lower the temperature level.

In addition, as shown in FIG. 1, the compressor 51 and expander 1 form a precooling refrigeration circuit 50. The main refrigeration circuit 60 having the cooler 3, as shown in FIG. 1, is constituted mainly of a Joule-Thomson circuit ( to be hereinafter called the J-T circuit ) which precools a refrigerant mainly of helium gas fed from a compressor 61 and is provided with a Joule-Thomson valve ( to be hereinafter called The J-T valve ) 62 which Joule-Thomson-expands the precooled refrigerant. The J-T circuit in FIG. 1 is provided with three first to third heat exchangers 63, 64 and 65 and first and second precoolers 66 and 67 for the refrigerant heat-exchanged at the first and second heat stations H1 and H2 at the expander 1 so as to obtain the coldness, the J-T valve 62 being interposed at the upstream side of the refrigerant with respect to the cooler 3.

The refrigerant gas fed from the compressor 61 is heat-exchanged at the first heat exchanger 63 with the refrigerant gas returning from the cooler 3 to the compressor 61, and cooled. Thereafter, the refrigerant gas is precooled by a first precooler 66 provided at the first heat station H1 (normally at 50 to 60K) of the expander 1, and then cooled by a second heat exchanger 64, and further precooled by a second precooler 67 (normally at about 15K) provided at the second heat station H2 (normally at 10 to 20K) of the expander 1. Then, the same is further cooled (normally at about 5K) by a third heat exchanger 65 and reaches the J-T valve 62 so as to be throttled and Joule-Thomson-expanded thereby. As the result, the refrigerant gas becomes a refrigerant in the gas-liquid mixing state of 4.2K at 1 atmosphere and is supplied to the cooler 3.

The liquid component of the refrigerant fed to the cooler 3 evaporates therein so that the latent heat of vaporization thereby cools the specimen mounting unit 2 at a very low temperature.

Also the refrigerant returning from the cooler 3 becomes saturated gas at about 4.2K so as to cool the refrigerant at the feed side by the heat exchangers 63, 64 and 65 and return to the compressor 61 in the state of warming.

The J-T valve 62 and the first to third heat exchangers 63, 64 and 65 referred to in the above explanation are housed in the vacuum chamber.

The vacuum container 5 contains therein the expander 1 so as to adiabatically expand therein the refrigerant gas, and is provided with a larger diameter barrel 9 having flanges 9a and 9b and a smaller diameter barrel 10 having flanges 10a and 10b, the flange 9a being fixed to a flange 11a at a base member 11, the flanges 9b and 10a being fixed to each other, and the flange 10b detachably supporting the open-close lid 6 so as to form a sealed container, thereby getting a vacuum in the container 5 by use of a vacuum pump ( not shown ).

Also, the vacuum container 5 constructed as above-mentioned constitutes by use of partition means to be discussed below a first vacuum chamber 12 positioned apart from the open-close lid 6 and a second vacuum chamber 13 positioned close thereto, the first and second vacuum chambers 12 and 13 being partitioned from each other in an airtight manner.

In a first embodiment of the invention shown in FIG. 2, the lower flange 10a at the smallest diameter barrel 10 is made smaller in an inner diameter than the smaller diameter barrel 10 so as to form an inward flange projecting radially inwardly. Meanwhile, an annular fixed wall 21, an outer cylinder 22 formed mainly of a telescopic bellows, an annular support 23 supporting the outer cylinder 22 at the upper end thereof, an annular top wall 24 fixed to the support 23, and an inner cylinder 26 having a bottom wall 25 and mounted to the inner periphery of the top wall 24, constitute a partition 20. The partition 20 is mounted to the inward flange at the smaller diameter barrel 10 through the fixed wall 21, whereby the first vacuum chamber 12 is separate in an airtight manner from the second vacuum chamber 13.

In other words, the first vacuum chamber 12 is composed of the interior of the larger diameter barrel 9 and a space formed by the outer cylinder 22 and inner cylinder 26 at the partition 20, and houses the expander 1.

The second vacuum chamber 13 is formed within the smaller diameter barrel 10, includes the exterior of the outer cylinder 22 and the interior of the inner cylinder 26, and houses the cooler 3 and specimen mounting unit 2 at the main refrigeration circuit 60, the main body 3a of cooler 3 being housed in an internal space of the inner cylinder 26.

The outer cylinder 22, support 23, top wall 24 and inner cylinder 26 having the bottom wall 25, which constitute the partition 20, form a movable unit vertically movable by means of telescopic movement of the outer cylinder 22. The bottom wall 25 is formed mainly of a heat insulator, and the lower portion of the main body 3a of the cooler 3 housed in the second vacuum chamber 13 perforates the bottom wall 25 and fixed thereto in an airtight manner. A pipe line 15 connected to an coil 14 wound on the main body 3a and having a lower coil portion 15a perforates the bottom wall 25 in an air-tight manner.

The support 23 is made larger in an outer diameter than the outer cylinder 22 and provided at the outer peripheral portion with a plurality of guide bores 23a into which a plurality of guide rods 27 fixed to the fixed wall 21 are inserted, thereby vertically guiding the movable unit.

In addition, each guide rod 27 is provided at an intermediate portion with a shoulder, a spring biasing the outer cylinder 22 in the extending direction is interposed between the support 23 and the shoulder, and a stopper 29 for restricting an extension stroke, in other words, the upward movement, of the movable unit, is adjustably mounted on the utmost end of each guide rod 27.

The expander 1 housed in the first vacuum chamber 12 is provided with a first thermal shield 30 of box-like shape mounted to the first heat station H1 in relation of thermal connection and enclosing the second heat station H2. The support 23 constituting the partition 20 is formed of a material of good thermal conductivity and supports a second cylindrical thermal shield 31 enclosing the cooler 3 and specimen mounting unit 2. At a portion of the support 23 facing the first vacuum chamber 21 are provided a plurality of thermally conductive rods 32 formed mainly of copper and downwardly extending. A heat conduction plate 33, which contacts with or departs from the first thermal shield 30 by vertical movement of the movable unit, is mounted to the lower ends of the rods 32, and between the first thermal shield 30 and the second thermal shield 31 is formed a thermal switch 34 which cuts off the thermal connection between both the shields 30 and 31 when the open-close lid 6 is open to exchange the specimen.

At the upper wall of the first thermal shield 30 is provided a heat conductive cylinder 35 having an inward flange 35a opposite to the heat conduction plate 33 so as to constitute together therewith the thermal switch 34. On the upper end of the second thermal shield 31, a lid 36, which is open to enable the specimen to be taken in or out, is detachably mounted. A joint pipe 37, through which dry gas is introduced into the second vacuum chamber 13 when its vacuum is broken, is mounted to the smaller diameter barrel 10.

Thus, the first vacuum chamber 12 housing therein the expander 1 and the second vacuum chamber 13 housing therein the coller 3 having the specimen mounting unit 2 are separate in an airtight manner from each other by the partition 20 constructed as above-mentioned. Hence, when the specimen is exchanged, the second vacuum chamber 13 need only break its vacuum, thereby minimizing the space required for breaking vacuum. Also, the specimen mounting unit 2 and cooler 3 need only be warmed up and cooled down, thereby reducing the warm-up time and cool-down time.

The specimen mounting unit 2 enclosed by the second thermal shield 31 is not affected by the heat radiation from the atmospher, thereby improving the adiabatic property. On the other hand, when the second vacuum chamber 13 breaks its vacuum due to the exchange of the pscemien, the heat may be transferred from the second thermal shield 31 to the second heat station H2 side at the expander 1 to thereby raise the temperature thereof in vain, but the thermal siwtch 34 is provided between the second thermal shield 31 and the first thermal shield 30 to selectively cut off the thermal connection, thereby avoiding the heat transfer from the second thermal shield 31 to the expander 1, resulting in that reduction of the cool-down time is obtained as expected.

In other words, during the cooling operation, as shown in FIG. 3, the outer cylinder 22 is biased by the spring 28 and extends to bring the heat conduction plate 33 in heat-conductive contact with the inward flange 35a, whereby the second thermal shield 31 thermally contacts with the first thermal shield 30 through the rods 32. Accordingly, during the operation, the specimen mounting unit 2 enclosed by the second thermal shield 31 can avoid an adverse effect of heat radiation from the enclosure of the vacuum container 5, resulting in a good heat insulation.

In a case where the open-close lid 6 is open for exchanging the specimen and the second vacuum chamber 13 has substantially atmospheric pressure by dry gas introduced into the chamber 13, as shown in FIG. 4, a pressure difference between the first vacuum chamber 12 and the second vacuum chamber 13 automatically contracts the outer cylinder 22 to disconnect the heat conduction plate 33 from the inward flange 35a, thereby almost eliminating heat transfer from the second thermal shield 31 to the just thermal shield 30. Hence, the cool-down time after exhanging the specimen is reducible because the expender 1 is not warmed in vain.

Figure 5:
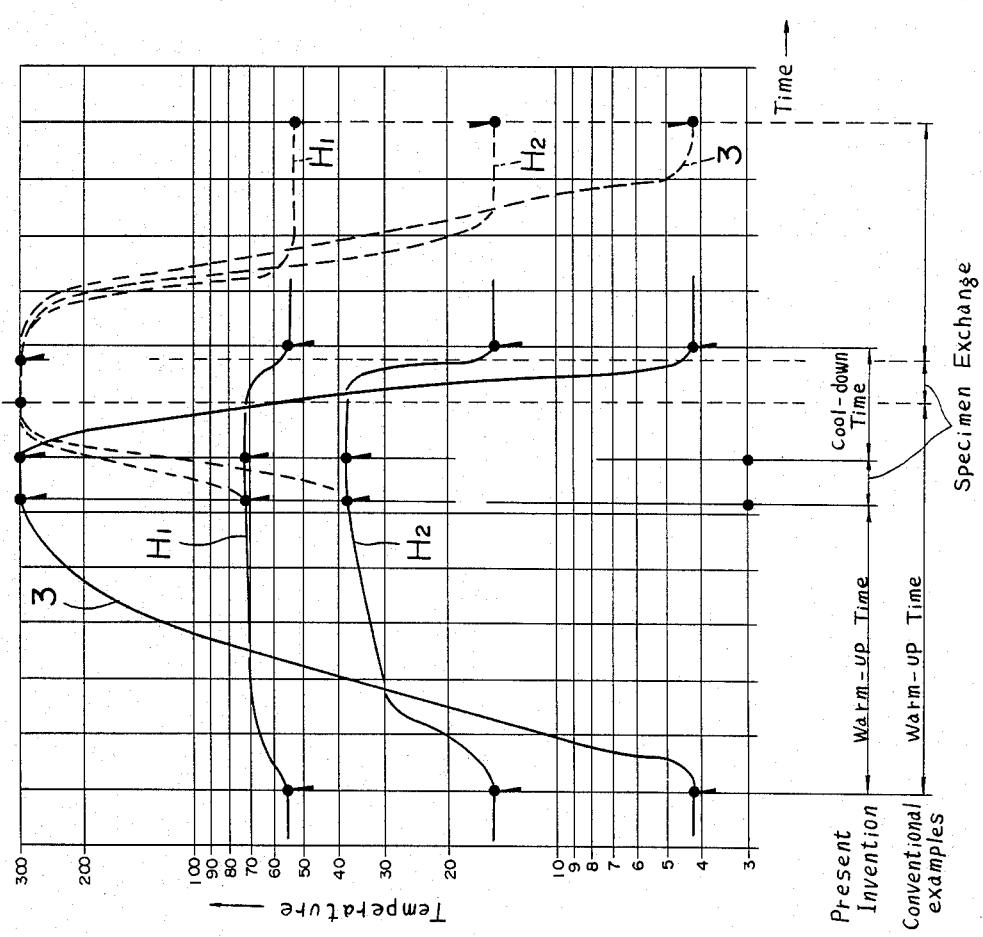
FIG. 5 is a graph showing temperature changes in a heat station and a specimen mounting unit.

Referring to FIG. 5, the above operational effect is clarified by temperature change at the respective heat stations H1 and H2 and specimen mounting unit 2. In detail, when the specimen is exchanged, the second vacuum chamber 13 only is broken of its vacuum, whereby the specimen mounting unit 2 and the cooler 3 attached thereto need only be warmed. Also, after exchanging the specimen, the cooler 3 need only be recooled, so that a temperature rise and recooling for the first and second heat stations H1 and H2 at the expander 1 are not required and the temperature change in the respective heat stations H1 and H2 can be restricted to a minimum. As a result, both the warm-up time and cool-down time for exchanging the specimen in the refrigeration system of the invention can be reduced more than the conventional one, thereby expecting an inprovement in a actual working efficiency of the refrigeration system.

Figure 6:
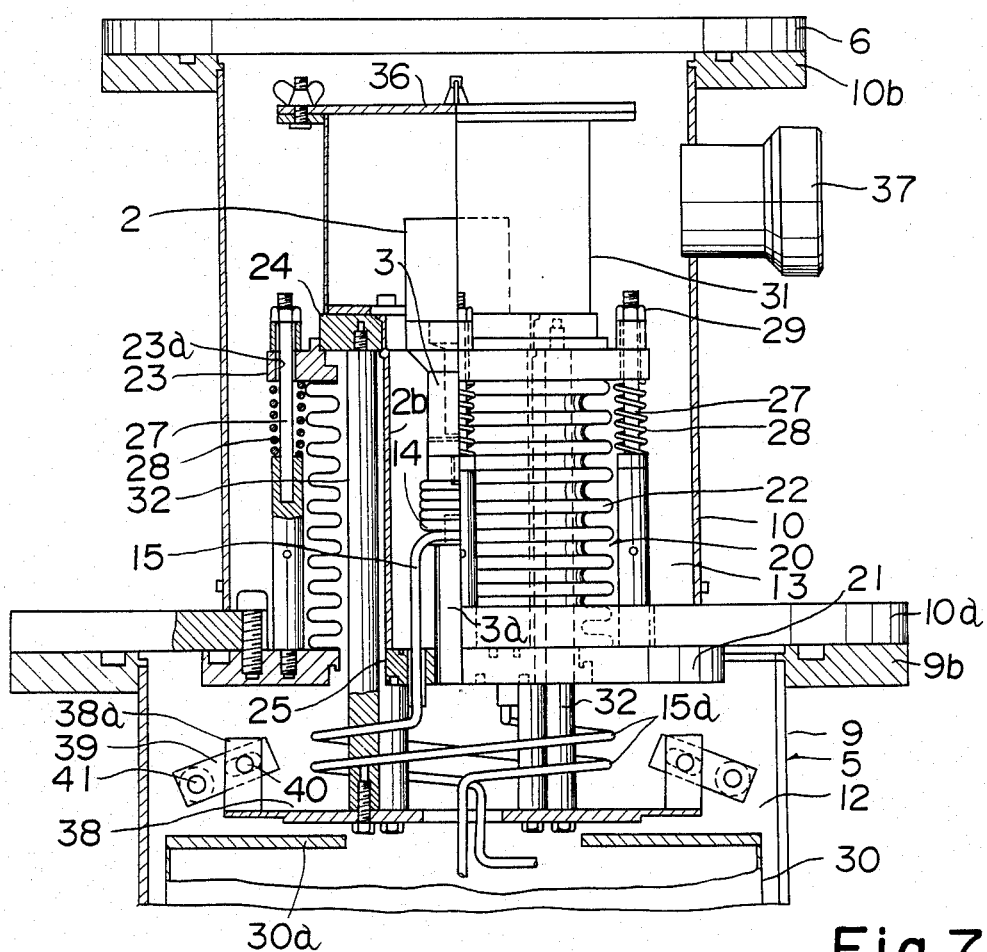
FIG. 6 is an enlarged sectional view of a second embodiment of the invention, corresponding to FIG. 4.

Alternatively, the thermal siwtch 34 in the first embodiment may be constructed as shown in FIG. 6.

In a second embodiment of the invention shown in FIG. 6, a heat conduction plate 38 attached to the lower ends of the heat conductive rods 32 is provided at the outer peripheral portion with a pair of rising elements 38a connected through pins 40 to arms 39 swingably supported to the larger diameter barrel 9, the arms 39 being forcibly swung by an actuator 41, such as a motor, so that the heat conduction plate 38 contacts with or departs from the top plate 30a at the first thermal shield 30, thereby forming a thermal switch for switching the thermal connection.

Figure 7:
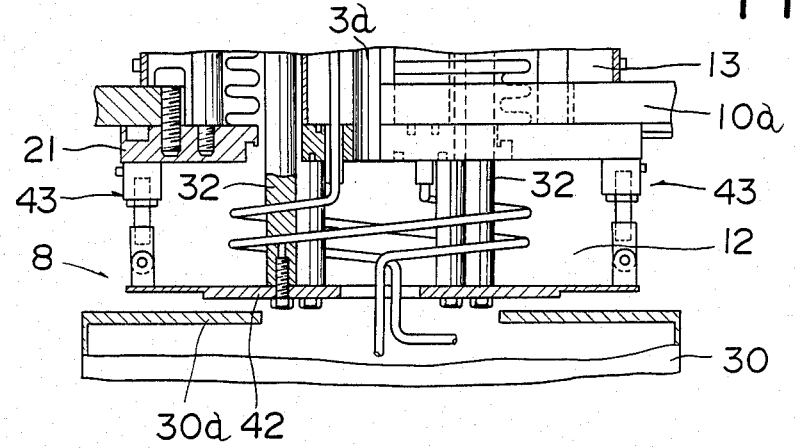
FIG. 7 is an enlarged sctional view of a third embodiment of the invention, showing the principal portion thereof only.

Alternatively, in a third embodiment of the invention as shown in FIG. 7, an actuator 43, such as a solenoid instead of the arms 39 in the second embodiment, may be interposed between the fixed wall 21 and a heat conduction plate 42 mounted to the lower ends of the heat conductive rods 32.

In the second and third embodiments, the thermal connection from the second thermal shield 31 to the first thermal shield 30 can be switched irrelevantly to degrees of vacuum at the two vacuum chambers 12 and 13, whereby just after a start of warm-up, in other words, when a pressure difference enough to downwardly move the movable unit at the partition 20 is not generated between the first and second vacuum chambers 12 and 13, the cooler 3 can thermally be cut off from the expander 1, thereby enabling the warm-up time to be further reduced.

Alternatively, in the aforesaid embodiments, the expander 1 need only have one or more heat stations.

Alternatively, a plurality of second thermal shields may be disposed at the second vacuum chamber 13.

Figure 8:
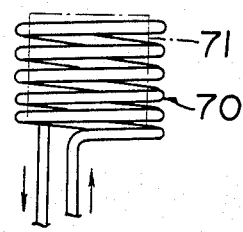
FIG. 8 is an illustration in part of another example of a cooler and the specimen mounting unit.

Furthermore, in all the embodiments, the coil 14 is wound onto the main body 3a of cooler 3 and the specimen mounting unit 2 is provided at the same, but as shown in FIG. 8, the cooler may alternatively be formed of a coiled pipe 70 only, so that a specimen 71 may be mounted directly thereon, thereby using the cooler also as the specimen mounting unit.

Also, the main refrigeration circuit 60 in the first embodiment in FIG. 1 may alternatively be omitted of the J-T valve 62. In this case, the third heat exchanger is not required.

As seen from the above, the present invention, when the specimen is exchanged, need only break a vacuum in the second vacuum chamber 13 and warm up and cool down the speciment mounting unit 2, thereby reducing the warm-up time and cool-down time, improving the actual working efficiency as the refrigeration system, and facilitating quick measurement of various physical quantities.

Furthermore, the second thermal shield 31 encloses the specimen mounting unit 2, thereby eliminating an adverse effect caused by heat radiation from the exterior and improving the adiabatic property.

Moreover, the thermal switch is provided between the second thermal shield 31 and the expander 1 to thereby solve the problem that heat transfer from the second thermal shield 31 to the expander 1 may cause a useless temperature rise. Hence, the cool-down time is reducible.

Although the invention has been described with refrenmce to several different embodiments, these embodiments are merely exemplary and not limiting of the invention which is defined solely by the appended claims.

What is claimed is:

1. A cryogenic refrigeration system for cooling and holding a specimen operated at the cryogenic level, provided with;
   (a) an expander having one or more heat stations and generating coldness by expanding a refrigerant gas, said heat stations being cooled by said coldness and held at a predetermined temperature level;
   (b) a main refrigeration circuit including a refrigeration stage having a specimen mounting unit for mounting thereon said specimen and cooling said specimen mounted on said specimen mounting unit and a heat exchanger for said refrigerant gas obtaining the coldness from said heat stations of said expander, said refrigerant gas obtaining the coldness from said heat stations being transferred to said refrigeration stage so as to cool said refrigeration stage at the cryogenic level, said specimen mounted on said specimen mounting unit being held at the cryogenic level;
   (c) a first vacuum chamber housing therein said expander, and
   (d) a second vacuum chamber housing therein said refrigeration stage and specimen mounting unit at said main refrigeration circuit, being separate from said first vacuum chamber, and provided with an open-close lid which is open to enable said specimen to be taken in or out with respect to said specimen mounting unit.

2. A cryogenic refrigeration system for cooling a specimen according to claim 1, wherein said main refrigeration circuit comprises a Joule-Thomson circuit provided with a Joule-Thomson valve which Joule-Thomson-expands said refrigerant gas precooled by said precooler, said Joule-Thomson valve being interposed at the upstream side of said refrigerant gas with respect to said refrigeration stage, so that refrigerant gas precooled by said heat exchanger is Joule-Thomson-expanded by said Joule-Thomson valve to be put in a gas-liquid mixing state, said refrigerant in said gas-liquid mixing state being evaporated, whereby latent heat of vaporization thereof cools said specimen.

3. A cryogenic refrigeration system for cooling a specimen according to claim 1, wherein one of said first and second vacuum chambers is formed in one vacuum container, said vacuum container being provided with partition means for partitioning said vacuum chambers in an airtight manner from each other.

4. A cryogenic refrigeration system for cooling a specimen according to claim 3, wherein said second vacuum chamber is provided with a thermal shield enclosing said refrigeration stage and specimen mounting unit of said main refrigeration circuit and thermally connecting with said heat station at said expander, so that between said thermal shield and said heat station is provided a thermal switch which cuts off thermal connection of said thermal shield with said heat station when said open-close lid is open to take in or out said specimen.

5. A cryogenic refrigeration system for cooling a specimen according to claim 4, wherein said partition means is provided with a movable unit which operates by an internal pressure difference between said first vacuum chamber and said second vacuum chamber generated when said open-close lid is open, said thermal switch being provided with a heat conduction member which is disconnected by operation of said movable unit to cut off the thermal connection of said thermal shield with respect to said heat station.

6. A cryogenic refrigeration system for cooling a specimen according to claim 5, wherein said partition means is provided with a fixed wall having a center bore and fixed to said vacuum container, an outer cylinder which is telescopic and mounted around said center bore of said fixed wall, an inner cylinder disposed inside said outer cylinder and having a bottom wall at the inside, and a top wall connecting said outer cylinder with said inner cylinder, said thermal shield and heat conduction member being mounted to said top wall.

7. A cryogenic refrigeration system for cooling a specimen according to claim 4, further provided with an actuator for connecting or disconnecting said thermal switch.

8. A cryogenic refrigeration system for cooling a specimen according to claim 4, wherein said first vacuum chamber is provided with a first thermal shield enclosing said heat station at said expander, said second vacuum chamber is provided with a second thermal shield enclosing said refrigeration stage and specimen mounting unit at said main refrigeration circuit, and connecting means for thermal connection is provided between said first thermal shield and said second thermal shield, said connecting means being provided with a thermal switch for cutting off said thermal connection when said open-close lid is open to take in or cut said specimen.

9. A cryogenic refrigeration system according to claim 1, wherein said refrigeration stage at said main refrigeration circuit is formed of a coiled pipe and serves also as said specimen mounting unit.

* * * * *